United States Patent
King et al.

(10) Patent No.: US 12,156,967 B2
(45) Date of Patent: Dec. 3, 2024

(54) VETERINARY VITAL SIGNS MONITOR WITH PRE-PROCEDURE CHECKLIST

(71) Applicant: Midmark Corporation, Versailles, OH (US)

(72) Inventors: Chris King, Troy, OH (US); Andrew W. Schultz, Jr., Lutz, FL (US); Jenny Flynn, Clearwater, FL (US); Guy Waterman, Versailles, OH (US); Joyce Ahrens, Versailles, OH (US)

(73) Assignee: Midmark Corporation, Versailles, OH (US)

( * ) Notice: Subject to any disclaimer, the term of this patent is extended or adjusted under 35 U.S.C. 154(b) by 907 days.

(21) Appl. No.: 17/166,554

(22) Filed: Feb. 3, 2021

(65) Prior Publication Data

US 2021/0236755 A1 Aug. 5, 2021

Related U.S. Application Data

(60) Provisional application No. 62/969,937, filed on Feb. 4, 2020.

(51) Int. Cl.
*A61M 16/01* (2006.01)
*A61B 5/00* (2006.01)
(Continued)

(52) U.S. Cl.
CPC ......... *A61M 16/01* (2013.01); *A61B 5/02055* (2013.01); *A61D 7/04* (2013.01);
(Continued)

(58) Field of Classification Search
CPC .. A61M 16/00; A61M 16/0093; A61M 16/01; A61M 16/022; A61M 16/024;
(Continued)

(56) References Cited

U.S. PATENT DOCUMENTS

| | | | |
|---|---|---|---|
| 2002/0004729 A1* | 1/2002 | Zak | G16H 70/20 |
| | | | 705/3 |
| 2007/0185390 A1* | 8/2007 | Perkins | A61B 5/02055 |
| | | | 600/300 |

(Continued)

*Primary Examiner* — Joseph D. Boecker
(74) *Attorney, Agent, or Firm* — Frost Brown Todd LLP

(57) ABSTRACT

Traditionally, vital signs monitors in the veterinary setting have been designed for use with human subjects that have simply been repurposed for use in the veterinary space. While some changes may be made to the human monitor to make it more amenable for veterinary use (e.g., changing the monitor display options from "adult" and "pediatric" to "large animal" and "small animal"), these changes are generally only done on a superficial level and thus omit significant veterinary-specific functionality that might otherwise be obtained. Further, vital signs monitors do not include a pre-procedure checklist or any functionality to increase safety awareness and allow clinics to ensure compliance with certain pre-procedure protocols. Accordingly, it is a purpose of the present invention to provide a veterinary-specific vitals signs monitor that overcomes these traditional limitations and increases the ease and efficiency with which veterinary care can be delivered.

11 Claims, 11 Drawing Sheets

(51) Int. Cl.
*A61B 5/0205* (2006.01)
*A61D 7/04* (2006.01)
*A61M 16/00* (2006.01)
*A61M 16/18* (2006.01)
*A61M 16/22* (2006.01)
*G16H 10/60* (2018.01)
*G16H 40/63* (2018.01)

(52) U.S. Cl.
CPC ........ *A61M 16/0093* (2014.02); *G16H 10/60* (2018.01); *G16H 40/63* (2018.01); *A61B 5/4821* (2013.01); *A61B 2503/40* (2013.01); *A61B 2505/05* (2013.01); *A61M 16/18* (2013.01); *A61M 16/22* (2013.01); *A61M 2202/0241* (2013.01); *A61M 2205/502* (2013.01); *A61M 2230/30* (2013.01); *A61M 2230/432* (2013.01); *A61M 2230/50* (2013.01); *A61M 2250/00* (2013.01)

(58) Field of Classification Search
CPC ................. A61M 16/18; A61M 16/22; A61M 2202/0241; A61M 2202/502; A61M 2250/00; A61D 7/04; A61B 2503/40; A61B 2505/05; G16H 10/60; G16H 40/63
See application file for complete search history.

(56) References Cited

U.S. PATENT DOCUMENTS

| | | | | |
|---|---|---|---|---|
| 2007/0255594 | A1* | 11/2007 | Muehlmeier | G16H 10/60 600/300 |
| 2014/0092089 | A1* | 4/2014 | Kasuya | G16H 50/50 345/420 |
| 2015/0277703 | A1* | 10/2015 | Davis | G06F 3/04817 705/2 |
| 2021/0225506 | A1* | 7/2021 | Mitchell | G16H 40/63 |

* cited by examiner

LARGE CANINE ANESTHESIA

PRE-PROCEDURE CHECKLIST

| | |
|---|---|
| X | Perform leak test on anesthesia machine |
| X | Check that APL valve is open on anesthesia machine |
| X | Confirm that $CO_2$ absorbent material is not expired |
| | Calculate intra-op drugs |
| | Calculate emergency drugs |
| | Confirm vaporizer is filled |
| | Check $O_2$ supply |
| | Check patient past complications |
| | Enter initials with keyboard |

SUBMIT

*FIG. 7A*

VETERINARY VITAL SIGNS MONITOR WITH PRE-PROCEDURE CHECKLIST

BACKGROUND OF THE INVENTION

The vital signs monitor is a critical piece of equipment in providing proper care to patients in the veterinary setting. Vital signs monitors can be used for various functions ranging from simple vitals collection as part of a routine patient checkup, to vitals monitoring during procedures ranging from minor dental treatments, to complex invasive surgery. Traditionally, vital signs monitors in the veterinary setting have been monitors designed for use with human subjects that have simply been repurposed for use in the veterinary setting. While some changes may be made to the human monitor to make it more amenable for veterinary use (e.g., changing the monitor display options from "adult" and "pediatric" to "large animal" and "small animal"), these changes are generally only done on a superficial level and thus omit significant veterinary-specific functionality that might otherwise be obtained. Further, safety awareness and accountability functionality for pre-procedure considerations are not present in any current vital signs monitor.

Given the above-noted observations, it is the goal of the present disclosure to provide a veterinary-specific vital signs monitor with numerous novel features for use in the veterinary care space. The vital signs monitor of the present disclosure may incorporate a pre-procedure checklist to increase safety awareness.

BRIEF SUMMARY OF THE INVENTION

The present invention relates to devices and methods, which, from a high-level perspective, serve to increase the ease and efficiency of veterinary healthcare delivery. By way of brief summary, the devices of the present invention include various embodiments of a veterinary-specific vital signs monitor capable of performing many useful functions. The methods of the present invention are directed at using the aforementioned devices in ways that increase safety, consistency, and efficiency in delivery of veterinary healthcare.

As a brief example of how the present invention may be utilized, in one of its preferred embodiments the present invention includes a pre-procedure checklist for increasing user safety awareness by causing a user to complete certain checklist parameters in the pre-procedure checklist and optionally entering the user's initials or other personal identifying information prior to unlocking or allowing access to the underlying vital signs monitor functionality.

The preferred embodiments of the present invention may also include veterinary-specific anesthesia case setup function that guides a user through best practices and necessary safety checks required in preparing to perform a veterinary procedure that involves the use of anesthesia. After the anesthesia case setup is complete, the device of the present invention can further provide veterinary specific dosage recommendations for pre-anesthesia medications, induction agents, and emergency medications should such be needed during the procedure. Finally, the device of the present invention could then be used to collect and display physiological signals from a patient while the patient is anesthetized.

While a number of more specific examples and a full description of the present invention are provided below, the example provided directly above should nevertheless be sufficient to allow one of ordinary skill in the art to appreciate the fundamental scope and objects of the present invention as well as to quickly gain a summary understanding of the utility provided by the devices and methods of present invention.

BRIEF DESCRIPTION OF THE DRAWINGS

FIG. 7A depicts another exemplary vital signs monitor display screen layout and options with respect to a pre-procedure checklist graphical user interface;

DETAILED DESCRIPTION OF THE INVENTION

Figure 1:
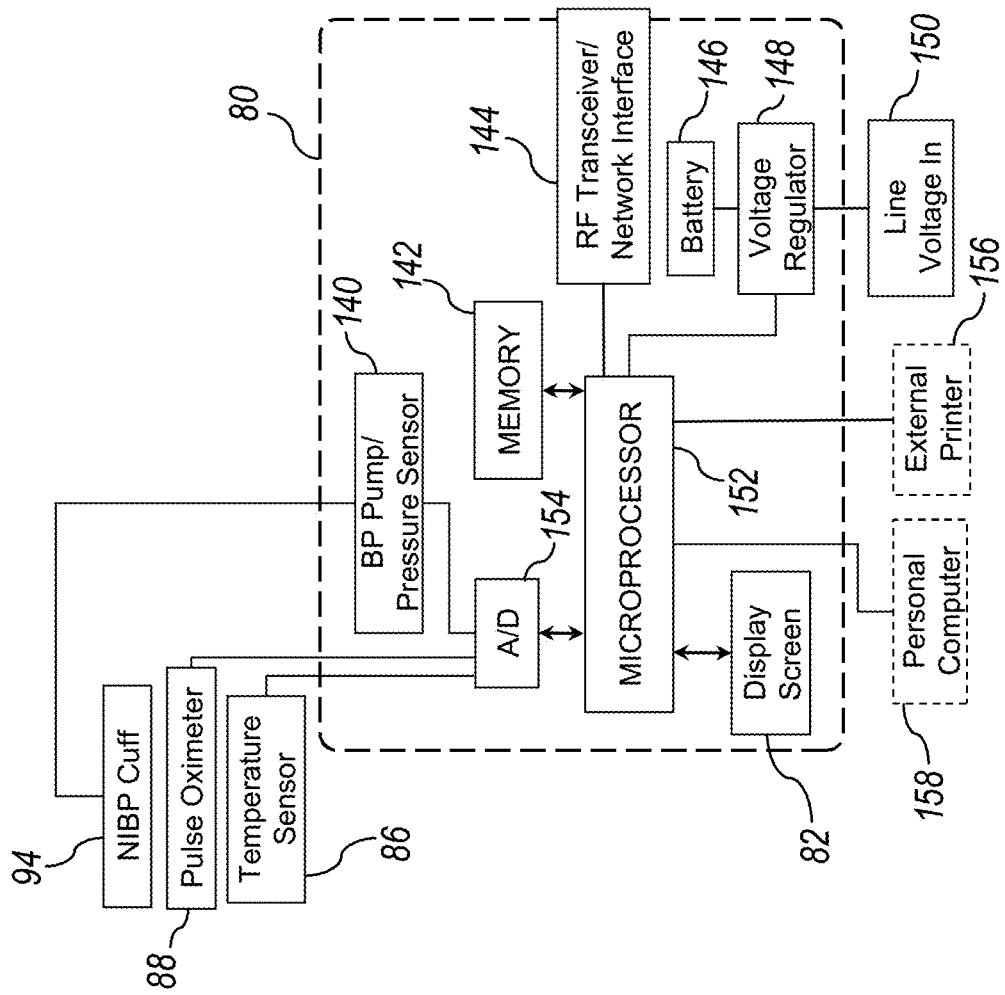
FIG. 1 depicts a block diagram illustrating the interconnection of various components of the vital signs monitor of the present invention.

The present invention is directed to a veterinary vital signs monitor ("VSM") and methods for use of the veterinary vital signs monitor disclosed herein. Broadly stated, the present invention provides a vital signs monitor for use in the veterinary care setting. The vital signs monitor described herein may take many forms and may include various feature sets that can be changed in order to better accommodate user needs.

To assist in clearly and effectively describing the present invention, it is helpful to broadly divide the invention into several elements. For purposes of describing the present invention, these elements can be most easily broken down as (1) the physiological sensors used in combination with the vital signs monitor, (2) the hardware and other physical components used in the vital signs monitor, and (3) the software, firmware or other instructions that are executed by the hardware of the vital signs monitor. It will be understood, however, that this categorical division of the present invention is intended only to aid in describing the invention and is not necessarily reflective of a required division of the above-noted elements when actually using the invention or practicing the associated methods.

The veterinary vital signs monitor disclosed herein is preferably capable of interfacing with, and collecting data from, a number of different sensors. Examples of these sensors include sensors for measuring blood pressure (both non-invasively and invasively), blood oxygenation, pulse rate, electrocardiogramals, end tidal carbon dioxide (EtCO2), temperature, respiration rate and/or effort, and anesthetic measurement sensors (e.g. infrared-based respiratory gas monitoring). These sensors can function in a variety of ways and can be fully analog, fully digital, or a combination of both.

By way of example of the different ways in which these sensors might function, the EtCO2 sensor may be either a mainstream sensor or a sidestream sensor. Further, electrocardiogramaignals may be collected using only three electrodes, or may alternatively be collected using 5, 7, or even 12 electrodes. Still further, the anesthetic sensor of the present invention could be configured to monitor and detect various anesthetics, including nitrous oxide, isoflurene, desflurane, enflurane, sevoflurane, and various haloalkanes. In addition, the anesthetic sensor may also include the ability to measure carbon dioxide concentrations. As a final example of how sensors of the present invention may function in different ways, the respiration sensor of the present invention can include indirect impedance or inductance-based measurement of respiration as well as direct measurement of respiration by measuring EtCO2. Thus, the EtCO2 sensor of the present invention can in certain embodiments serve as both a respiration sensor and a CO2 sensor. It will be noted that the above examples are not given by way of limitation, but rather serve only to illustrate some of the many ways in which the above-noted sensors may function as part of the present invention.

The veterinary vital signs monitor disclosed herein preferably includes a housing in which sufficient hardware can be placed to allow the vital signs monitor to at least acquire, process, store, and display physiological data to a user. The housing in which the processing and other hardware are placed preferably comprises a durable material capable of tolerating frequent use as well as providing substantial impact resistance. Accordingly, materials that can be used to form the housing of the VSM include various lightweight metals or metal alloys (e.g., aluminum, aluminum alloys, magnesium alloys, and the like), various polymers (e.g., polyvinylchloride, acrylonitrile, polyurethanes, polypropylene, polyethylene, and the like), or a combination of these in the form of composite materials.

Since the VSM of the present invention must be able to collect and display physiological data, the VSM preferably includes at least a microprocessor, a memory, and input and output ports or channels for sending and receiving data to the various sensors used with the VSM as well as to other devices, including display devices and data storage devices at locations remote from the VSM. The VSM memory, in addition to being capable of storing data generated by the processor or received via the input port(s), is used to store instructions including commands and processes followed by the processor (discussed in greater detail below). The VSM memory is preferably digital memory capable of storing digitized data. The VSM memory is also preferably at least partially comprised of non-volatile digital memory.

The input and output ports, or communications port(s), of the VSM can preferably send and receive data to and from the VSM by either wired or wireless transmission or a combination of the two and can handle and produce either digital or analog data. Examples of different types of communications ports used in the VSM of the present invention include, but are not limited to, serial ports (e.g., various types registered jack ports such as RJ11 or RJ45 format using RS232, IEEE 802.3, or other similar communication standards), universal serial bus (USB) ports, and radio frequency (RF) network interface controllers with their associated antennas (hereinafter, wireless ports), in addition to the various types of input ports used in connecting the above-noted sensors to the VSM.

Where appropriate, the communications ports of the VSM are preferably capable of interacting with and transmitting data between a number of different other devices connected through direct hard-wired connections or any type of network, including, for example, local area networks (LAN), personal area networks (PAN), the Internet or a combination of these. If wireless transmission of data is implemented through a wireless port, it is preferable that the VSM include hardware that allows it to communicate wirelessly using any desired or appropriate protocol. Examples of protocols that could be used by the VSM to communicate wirelessly through a communication port include, but are not limited to, the Wireless Medical Telemetry Bands, in the 608-614 MHz, 1395-1400 MHZ, or 1427-1432 MHz ranges, as well as ZigBeeR, Bluetooth®, or IEEE 802.11 communication protocols.

In certain embodiments of the present invention the VSM preferably has more than one input and/or output port(s). In embodiments of the present invention in which the VSM uses multiple communications ports, it is not required that all ports be of the same type. For example, in certain preferred embodiments, the VSM may have multiples of each of USB ports, Ethernet ports, serial ports, various sensor ports, and wireless ports, or such other ports as may be desirable for communication of analog or digital data to or from the VSM. Multiple communications ports allow the VSM to both send and receive information more effectively and efficiently as well as to easily communicate with numerous different devices. By way of example, one can envision an instance in which the VSM is simultaneously receiving data from physiological sensors connected to the VSM, processing this data, then communicating this data to an external storage location using radio frequency communication.

In certain preferred embodiments the VSM of the present invention is capable of communicating with an external printer and sending data to the printer so that a paper copy of the data can be obtained. For example, a user may wish to print a record of a subject's ECG measurements and may thus advantageously print such a record directly from the VSM. In still other preferred embodiments of the present invention, the VSM may include an integrated printer that allows printing of physiological recordings directly from the VSM itself.

In still other preferred embodiments of the present invention, the VSM includes an audio output channel that preferably connects to a speaker that is integrated into the VSM housing in such a way that audible signals generated by the speaker can be heard by the user.

In embodiments of the present invention in which the VSM is used to measure blood pressure, the VSM preferably includes a pump capable of using atmospheric air to pressurize a sphygmomanometer cuff to pressures sufficient for accurate measurement of systolic and diastolic blood pressures across various genera and/or species of animals. Blood pressure measurement is preferably performed using pressure sensors pneumatically connected with the sphygmomanometer cuff and accompanying algorithms executed by the VSM processor that can determine a subject's blood pressure without the need of a stethoscope and without requiring significant veterinarian or other clinician involvement. In still other embodiments of the present invention, the VSM includes appropriate input ports and electronic hardware to allow the VSM to measure blood pressure using an invasive blood pressure sensor placed in one of a patient's arteries.

In embodiments of the present invention in which the VSM is capable of measuring pulse rate and/or blood oxygenation, these measurements are preferably accomplished using a transmission-based infrared oximeter sensor connected to the processing system of the VSM. One example of a preferred transmission-based infrared oximeter sensor compatible with the VSM of the present invention is the Nellcor™ Oximax™ line of pulse oximeter sensors. In other preferred embodiments of the present invention, measurement of blood oxygenation and pulse rate can be accomplished using a reflectance-based infrared oximeter sensor. It will further be noted that in still other embodiments of the present invention, measurement of pulse rate need not be accomplished using an oximeter sensor, but can instead be accomplished using the above-mentioned sphygmomanometer cuff, ECG sensors, or other types of pressure sensors.

In embodiments of the present invention in which the VSM is capable of measuring temperature, temperature measurement is preferably accomplished using a thermistor-based temperature probe. However, in still other preferred embodiments temperature can be measured from a subject using optically-based technologies, such as temporal artery or tympanic membrane temperature probes connected to the processing system of the VSM.

The VSM of the present invention preferably further includes a display screen for displaying data to the user of the VSM. Data that can be displayed on the screen of the VSM includes, but is not limited to, the measurements obtained using any of the above-noted physiological sensors. Because the VSM can connect to other devices over the types of networks mentioned above, data displayed on the screen of the VSM can also include data pertaining to a subject's health, such as data obtained from the subject's medical records, including data relating to medical problems previously experienced by the subject.

The display screen of the VSM can be either liquid crystal display (LCD) or light emitting diode (LED) based, or a combination of the two. Thus, in various embodiments, the display screen of the VSM can be a passively lit monochrome LCD display, a backlit color LCD display (including LCD displays that use LEDs for backlighting), or an LED-only display, including the use of organic LEDs. In addition, the display screen of the VSM can also be a touch-sensitive display screen. A touch-sensitive display screen allows the user to manipulate data that is displayed on the screen and can also allow the user to add additional data to a subject's medical record, or add additional details to the physiological measurements collected from the subject using the VSM. A touch-sensitive display screen also allows the user to easily adjust the system settings of the VSM (e.g. units in which measurements are displayed). If a touch-sensitive screen is implemented, it can be either a capacitance-based touch-sensitive screen or a resistance-based touch-sensitive screen. In still other embodiments, the VSM may receive user input such as that described above via a keyboard, mouse, input buttons or dials incorporated with the VSM, or other input means. In this case, a display screen would be required on the VSM, however, this display screen would not necessarily need to be touch-sensitive since data entry and manipulation of data, or changing the type of data displayed, could be accomplished using the independent input means just noted.

In still other preferred embodiments of the present invention the VSM can connect to a personal computer through one of the communication ports listed above. In this embodiment the personal computer preferably includes appropriate software to allow it to effectively communicate with and transfer data between the VSM and the personal computer. Also in this embodiment, the display of the personal computer can be used to display data collected by the VSM, and the keyboard, mouse, or other input means attached to the personal computer can be used to manipulate this data, add additional data to a subject's medical record, add additional details to the physiological measurements collected from the subject using the VSM, or change the VSM settings.

In addition to the above-noted features, the VSM preferably also includes a power source for powering the processing system of the VSM as well as providing power, where needed, to the sensors and/or other devices used in combination with the VSM. The power source can include line voltage (e.g. 120V, 60 Hz A/C; 220V, 50 Hz A/C) filtered through appropriate regulators, or can include a rechargeable battery that is charged by the use of appropriate regulators connected to line voltage. If a rechargeable battery is used, it is preferably a nickel-cadmium, nickel-metal hydride, lithium-ion, lithium-ion polymer, or lithium iron phosphate battery.

Additionally, as briefly mentioned above, in certain preferred embodiments of the present invention the VSM includes hardware and software that allow the VSM to connect to and interact with the electronic medical record (EMR) and/or practice management software of the facility in which the VSM is located. In this way, the VSM can both retrieve existing data from, and send newly recorded data to, the EMR or practice management system of the facility in which the VSM is located. By providing the ability to electronically record and transfer physiological measurement data, the VSM can eliminate the time-consuming manual entry of such data into an EMR system.

As mentioned above, the VSM of the present invention preferably includes a number of software and firmware components (hereinafter collectively referred to as "software"). These software components are typically stored as a set of instructions in the digital memory of the VSM and/or in digital memory at a remote server that can be accessed by the VSM. The various functions of this software are explained in greater detail below.

Preferably the VSM of the present invention contains software that allows the VSM to both send and receive data to and from remote locations. This communication can be accomplished using various standard ports or the above-mentioned wireless port. Preferably data is sent and received between the VSM and other devices using wireless or direct hard-wired connections in combination with a larger network, including, for example, local area networks (LAN), personal area networks (PAN), the Internet, or a combination of these.

One feature of certain embodiments of the VSM of the present invention is the ability of the VSM software to allow one to remotely access the VSM. Specifically, in certain embodiments of the present invention the VSM includes software and hardware necessary to allow one to connect to and communicate with the VSM from a remote location using a personal computing device such as a laptop computer or the like. Typically this will involve the use of standard communication protocols known to those of ordinary skill in the art. Preferably, these communication protocols use encryption methods (e.g., transport layer security, secure sockets later, and the like), also known to those of ordinary skill in the art, to maintain security of the information communicated between the VSM and the remote device. In certain embodiments of the present invention, this remote connection and VSM software functionality can allow the remote user to view the contents of the VSM display screen and even control VSM settings from a remote location.

In still other embodiments, the VSM can preferably be configured to allow transfer of patient data between the VSM and a host server at a remote location. As mentioned above, such a feature allows the VSM to display patient data and also allows physiologic data recorded from a subject using the VSM to be uploaded to the remotely located on the host server. By way of example, one can envision an instance in which a group of several commonly-owned practices located at separate geographic locations share a common electronic medical record and practice management system, the data from which is located on a shared remote server. In this example, the VSM of the present invention is capable of communicating with the shared remote server and can thus receive data regarding a patient's medical history from the remote server, as well as the patient's status within the practice management software. By status within the practice management software it is meant that the VSM can receive information regarding when a patient's next scheduled appointment is, whether a patient is "checked-in" for a current appointment, and the like. In this way, the VSM could be used to produce a current list of "checked-in" patients from which the patient currently being examined could be selected from the VSM display screen and that patient's physiologic data could then be securely transferred to and recorded on the remote server. This data could then be accessed and retrieved at a later point using the VSM and processed by the VSM to provide a view of physiologic measurements for a single patient over multiple visits through an extended period of time. When used in this manner, the VSM can also eliminate the need for a separate personal computer in the examination room.

In another preferred embodiment, patient information may be stored directly on the memory of the VSM device. In this embodiment patient information may be stored as a copy of patient information that is stored at a remote server, allowing the VSM to be used to record and store a patient's physiological measurements without needing to be connected to a remote server. Additionally, if the VSM is then subsequently connected to the remote server, the new data can be communicated to the remote sever and the copy of the patient's data located on the remote server updated with the new data.

In still other embodiments, the ability of the VSM to connect with and communicate with other devices also allows the VSM to provide remote diagnostic functionality in which an individual skilled in repair and troubleshooting of the VSM can gain remote access to the VSM in order to repair or diagnose potential operating issues with the VSM. This same feature also allows the software and/or firmware on the VSM to be updated remotely and allows both the manufacturer and the user of the VSM to ensure that the VSM includes the most recent versions of software and firmware.

Finally, the ability of the VSM to connect with and send data to other devices allows the user of the VSM in certain preferred embodiments to order replacement supplies directly from the VSM interface or display screen. In this embodiment, the VSM includes the ability to securely connect to a server (either via the Internet or other similar means) that allows the user to communicate with entities that provide supplies to the user, pay for these supplies, and direct shipping and delivery of these supplies to the user. Supplies ordered via the VSM could include, for example, replacement ECG electrodes, replacement respiratory sensors, and the like. Still further, in certain embodiments of the present invention, the VSM can include a software feature that allows the VSM to track the type and volume of procedures for which the VSM is used and to recommend replacement products based on this data. For example, if the VSM software indicates that the VSM has been used for a certain number of anesthetic-based procedures, the VSM software could suggest that $CO_2$ absorbent material or $CO_2$ sensors be replaced as part of a standard maintenance interval.

Other VSM features provided at least in part by the VSM software include a veterinary-specific user interface that allows the user to select between settings for "Small Animal" or "Large Animal" and in certain preferred embodiments allows the user to further select from genus-specific or species-specific preprogrammed configurations (e.g. preset programs for birds, rodents, feline patients, equine patients, etc.). Such preprogrammed configurations significantly increase the ease of use of the VSM of the present invention by eliminating the need for a user to take the time-consuming step of separately determining genus- or species-specific recommended VSM settings and typical ranges of physiologic measurements for the various genera or species with which the user is concerned.

The software and memory of the VSM can preferably also be used to accept and store user-customized profiles for later recall and use by specific individual users. Thus, by using this feature a user can set his or her preferences (e.g. preferred screen layout, preferred alarm limits, preferred units of measurement, etc.) and then save these preferences to a user-specific profile that can then be loaded when the user next utilizes the VSM. As will be understood, such a feature is especially useful in a setting where multiple individuals share use of a single VSM.

Additionally, the VSM of the present invention can, in certain preferred embodiments, include preprogrammed configurations for specific functions, such as diagnostic only functions and anesthesia specific functions. For example, the VSM in certain embodiments includes a preprogrammed setting for diagnostic use only. Accordingly, a user could select this setting when the VSM is to be used only for routine measurements such as basic blood pressure measurements, standard ECG measurement procedures, and the like. In the alternative the user could select, for example, the anesthesia preprogrammed setting when using the monitor in situations that require anesthesia. By way of example, selection of the preprogrammed setting for anesthesia can cause setting of $EtCO_2$ as one of the primary waveforms displayed on the VSM, default ECG settings to be changed to 5-lead ECG, and automatic non-invasive blood pressure measurement that occurs at a preset interval, among other changes to the VSM that would be beneficial if the VSM were to be used in combination with anesthetic.

The software of the VSM of the present invention further preferably allows the user to input a number of veterinary-specific (including genus- and species-specific) alarm limits and also preferably comes preprogrammed with recommended alarm limits. Alarm limits can be set for parameters such as hypotension, hypertension, hypocapnia, hypercapnia, respiratory rate, pulse rate, oxygen saturation, and other critical physiological parameters monitored using the VSM of the present invention. By providing preprogrammed alarm limits, ease of use of the VSM is increased for cases in which preprogrammed alarm limits are suitable. However, by also allowing a user to modify these alarm limits and specify their own desired alarm limits, flexibility of use is maintained. It will be noted that this flexibility is especially important in veterinary practice due to the wide range of patients on which the VSM might be used.

Along with alarm limits, the VSM is also capable of producing alerts to notify the user of the VSM that an alarm limit has been exceeded, or of other conditions that require the user's attention. These alerts include traditional tonal alerts as well as voice alerts that comprise a recording of a human voice stating the cause of the alert. The use of voice alerts can be especially useful when the VSM is used in procedures requiring anesthesia, since it eliminates the need for the veterinarian or other clinician to have to visually inspect the VSM in order to discover the cause of the VSM alert.

In addition to tonal and voice alerts, the software of the VSM preferably further provides informational displays to the user that assist the user in troubleshooting the cause of an alert and then determining an acceptable method of addressing the cause of the alert. By way of example, in one preferred embodiment of the present invention the VSM includes a touch-sensitive display screen and the software component includes algorithms that determine the cause of the alert and then provide a small information icon on the VSM display screen. If the user then touches or otherwise selects this icon, a pop-up screen appears that provides information about the cause of the alert and a suggested method(s) of addressing the alert. For example, if hypotension was the cause of the alarm, the message would indicate such and may include directions to increase intravenous fluid delivery rate, decrease anesthesia, increase oxygen delivery, or the like.

In still other embodiments of the VSM, the blood pressure monitoring incorporates adaptive technology to make successive readings more efficient for the caregiver, and more comfortable for the patient. The initial inflation for one embodiment of the VSM designed for veterinary use is 150 mmHg, thus the blood pressure cuff is so inflated, and the step-down release of pressure will result in measurements of systolic, mean and diastolic blood pressure. In cases where the patient's actual systolic pressure is higher than 150 mmHg, the initial step down will fail to obtain a reading, and the VSM will adapt by beginning the next assessment 30 mmHg higher than the last reading attempt and step down from there. It will continue increasing the beginning inflation pressure until it successfully obtains a reading. Successive readings will begin 30 mmHg higher than the last attempt or actual reading, thus eliminating the initial discovery process once a reading has been obtained. This function will be reset with each new patient, or following the power off/power on cycle of the VSM itself.

The software of the VSM also preferably provides the VSM with the ability to enter a non-invasive blood pressure screening mode that takes a series of measurements as a result of input from the user or as the result of a physiologic signal being outside of safe limits. For example, if the VSM is being used for anesthesia and a hypotension alarm is triggered, the VSM would enter an automated blood pressure monitoring mode in which blood pressure measurements are automatically repeated at predetermined intervals and for a predetermined period of time (e.g. every minute for five minutes). As an additional example, in non-anesthesia settings the VSM software can provide a non-invasive blood pressure screening mode that allows for automatic averaging of a series of consecutive blood pressure measurements. In one preferred embodiment, 5-7 consecutive measurements are obtained and then averaged using algorithms to determine average systolic pressure, diastolic pressure and mean arterial pressure (MAP). More specifically, one preferred approach to producing average pressure measurements includes taking a series of consecutive blood pressure readings, determining the difference between individual consecutive systolic pressure, diastolic pressure, and MAP measurements (i.e., the difference between a first systolic pressure measurement and the subsequent consecutive systolic measurement, etc.), summing these differences, discarding the reading with the largest sum of differences, and then taking an arithmetic average of the remaining measurements to determine average values for systolic pressure, diastolic pressure and MAP. These average values can then be displayed on the display screen of the VSM. The ability to produce average blood pressure values is especially useful in the veterinary setting since it is often difficult in this setting to have the subject maintain a stationary position while a blood pressure measurement is being obtained. Thus, averaging blood pressure measurements provides a convenient way to minimize measurement errors that result from movement artifact or other inconsistencies encountered when interacting with veterinary patients.

In some versions of the VSM, five consecutive blood pressure measurements are obtained. The measurement with the MAP that deviates the most from the MAP of the other four readings is then discarded. The remaining four blood pressure measurements are thereafter averaged together, with the resulting average blood pressure measurement data displayed to the user.

In still other embodiments of the present invention the software includes an algorithm for calculating a parameter index that is reflective of overall patient wellness during a procedure in which the patient is anesthetized. Specifically, the parameter index preferably includes a weighted combination of any or all of a subject's pain index, heart rate, respiratory rate, blood pressure, temperature, ECG measurements, end tidal CO2 measurements, and anesthetic delivery rate. By providing an index value based on a weighted combination of various physiological parameters and then displaying this value on the VSM display screen the VSM of the present invention can provide a consistent and efficient metric for determining how well a surgery is proceeding and how well a patient is tolerating anesthesia. By way of example, in one preferred embodiment, heart rate variation, blood pressure variation and end tidal CO2 measurements are normalized and then placed into a weighted combination that provides a final parameter index on a scale of 1 to 10. In this example, blood pressure variation is normalized and assigned a value from 1 to 4. The same is done for end tidal CO2 variation. Heart rate variation is normalized and assigned a value from 1 to 3. These normalized values are then summed to provide a parameter index value between 1 and 10. A higher value on this scale indicates that a subject is more stable and that a procedure is thus proceeding more positively than it might otherwise be. It will be recognized that this approach or others more complex but similar to it may be used with different variables or a greater number of variables and still fall within the scope of the present invention.

The VSM of the present invention includes a number of additional features that make it especially useful in applications that require a patient to be anesthetized. One of these features is a veterinary-specific drug dosage calculator. This feature allows the user to quickly retrieve recommended dosages of pre-anesthesia medications, induction agents, fluids, and emergency medications based on user inputs of genus and/or species, weight, risk status of the patient and other similar inputs. This dosage information is preferably stored in the memory of the VSM but may in certain other preferred embodiments be stored on a remote server and retrieved using the methods discussed herein. Storage and retrieval of the dosage information is conducted according to known database management and indexing methods.

In some versions of the VSM, the user can access catalogs for CO2 and ECG waveforms to allow for quicker interpretation of abnormal waveforms which may occur during procedures while patients are under anesthesia. The feature allows for the user to access the catalog from the main display without the need to enter a separate menu. Users have the ability to use the touch screen to advance through the catalog to compare its sample waveforms with the patient's actual physiological waveforms in real time to identify certain abnormalities. This feature can also be turned on and off in the associated set up menus. This is intended to promote proper monitoring and increase patient safety."

Yet another feature of the VSM that is useful when a patient is to be anesthetized is the VSM software providing interpretive CO2 waveforms and trending. The VSM software thus preferably also includes algorithms that are able to track CO2 trends and provide warnings and alerts to the VSM user in cases of erroneous placement of endotracheal tubes, airway obstructions, deterioration of airway muscle tone, and the like. The methods for performing such trend analysis are well known in the art, though in the past these methods have not been applied as effectively to veterinary practice as they could have been.

The VSM software further preferably includes veterinary-specific ECG analysis algorithms that use genus-specific and/or species-specific ranges for heart rate, QRS duration and ECG waveform and amplitude, and thus increase accuracy of heart rate measurement by eliminating double-counting. The use of veterinary-specific ECG algorithms also allows for more accurate identification of cardiac arrhythmias or poor cardiac performance across different genera and/or species and thus more timely and accurate alerts to the user of the VSM. In one preferred embodiment of the present invention, instead of species specific ranges the VSM includes two broad sets of ECG parameters, grouped into "large animal" and "small animal" categories. In this embodiment the large animal and small animal ECG alarm parameters are as follows:

Large Animal Heart Rate Trigger
   Minimum heart rate=15 beats per minute (asystole at 4 seconds)
   Maximum heart rate=300 beats per minute
   Double count limit=315 beats per minute (half counting occurs above 315 beats per minute
   QRS trigger window=60 to 120 milliseconds
   QRS amplitude=0.15 to 5.0 millivolts (Lead I)
Small Animal Heart Rate Trigger
   Minimum heart rate=15 beats per minute (asystole at 4 seconds)
   Maximum heart rate=300 beats per minute
   Double count limit=315 beats per minute (half counting occurs above 315 beats per minute
   QRS trigger window=25 to 60 milliseconds
   QRS amplitude=0.15 to 5.0 millivolts (Lead I)

It will be understood that genus- or species-specific ECG parameters would function similarly to the more generalized "large animal" and "small animal" parameters just listed.

The VSM software further preferably provides an anesthesia case setup function. When selected by the user, the anesthesia case setup function provides an on-screen safety and setup checklist that guides the user through best practices for setting up the VSM for use in procedures that require anesthesia. Instructions provided to the user include instructions for properly connecting sensors to the patient and to the VSM, running a pressure check on the anesthesia machine to be used in the procedure, and tips on proper administration of anesthesia, among other relevant items.

The VSM software of the present invention still further preferably provides the user with the ability to print or download (e.g. to a flash memory device via one of the VSM USB ports) a procedure report that documents patient data, anesthetic(s) used, equipment settings, physiological signal measurements, trending analysis of physiological signals, clinician notes, and the like. In one embodiment of the present invention, this procedure report is preferably generated automatically at the close of a given procedure and copy automatically saved to a patient's electronic health record.

In still other embodiments of the present invention, the VSM software includes a resettable maintenance timer or counter that provides reminders to the user about maintenance functions such as changing CO2 absorbent material, or having the anesthetic vaporizer periodically serviced. In this way, the VSM can provide an easy and convenient method for ensuring that the user keeps up on maintenance of key third party components frequently used with the VSM.

An additional feature that can be included in certain embodiments of the present invention is a remote control for use with the VSM. The remote control can be wired, can use Bluetooth® or other radio frequency technology, or can be infrared based and preferably allows a user to control various functions of VSM (e.g., alarm silencing, display toggle between data sets, and the like) from a remote location. The remote is useful in instances in which the VSM is located beyond reach of the clinician since it allows the clinician some measure of control of the VSM from wherever the clinician is currently located within the clinical space. The remote control is preferably tightly sealed and implements membrane switches or other switches and a remote housing that lend themselves effectively to, and have been shown to withstand, frequent chemical sterilization.

In addition to the features already addressed above, the VSM of the present invention preferably also includes a demonstration mode, a teaching and training mode, and, where appropriate, on-board training tutorials. If the demonstration mode is selected by the user the VSM displays wave forms and values that would typically be encountered when using the VSM in either the anesthetic or diagnostic settings. Thus, the demonstration mode can be useful in demonstrating functions of the VSM to a potential purchaser or familiarizing a new user with the VSM. In training mode, the VSM software provides several preset situational scenarios (e.g. hypertension, hypocapnia) that allow a user to select and respond to informational prompts and reflects changes in the wave forms displayed on the VSM display screen as a result of the user's response(s).

The training mode can also be paired with on-board training tutorials that interactively take the user through the various features offered by the VSM (e.g., proper set-up for use in anesthesia, proper methods for consistently obtaining accurate blood pressure measurements with the VSM, and the like) using text, video, and audio voice-over. It will further be noted that it is envisioned that the training mode may also be used as a conduit to provide approved continuing education training to veterinary clinicians who use the VSM. While the above-noted content can be stored directly on the VSM memory, it can also, where appropriate, be retrieved from a remote server using the methods discussed elsewhere herein and subsequently displayed on the VSM screen. All of these features serve to increase the likelihood that the VSM of the present invention will be used properly and effectively and also increase the ease with which a clinician can become proficient at using the VSM of the present invention, in addition to increasing the utility of the VSM.

As indicated in the above description, the VSM of the present invention is capable of displaying various information on the display screen-whether this is the displaying of real-time physiological measurements or recalling previously recorded data. It will be noted that the information displayed on the VSM display screen, and the way in which it is displayed, can be controlled at least in part by the user of the VSM. For example, when used in anesthesia monitoring the software of the VSM allows the user to organize waveform channels in the order desired (e.g. EtCO2 waveform displayed on the top of the display screen with ECG waveform positioned on the bottom of the display screen).

A pre-procedure checklist feature may also be incorporated into the VSM. In general, the pre-procedure checklist provides a list of items on the VSM display screen that a user may review and acknowledge prior to beginning a procedure in which the VSM will be used. In certain embodiments, the pre-procedure checklist may serve only as a simple reminder to a user. However, in other embodiments, the pre-procedure checklist may function to prevent access to the underlying traditional functionality of the VSM until each item in the checklist is acknowledged and some form of personal identifying information is entered. For example, the pre-procedure checklist may prompt the user to perform a leak test on the anesthesia machine, confirm that carbon dioxide absorbent material is not expired, and confirm that an anesthesia vaporizer has been filled. After these checklist parameters are attended to, the user checks a box or otherwise acknowledges their completion. Thereafter, the user may enter his/her initials into a text box and submit the pre-procedure checklist. The user's initials are stored for later review if necessary, possibly with a timestamp or other information. Thus, the pre-procedure checklist increases safety awareness and can allows clinics to track user compliance with such checklists.

Turning now to a description of the figures, in FIG. 1 there is shown a schematic block diagram illustrating various components of the VSM that are included in certain preferred embodiments of the present invention. The components included within the VSM of the present invention are located within box represented by dashed line 80.

The VSM 80 includes a VSM memory 142, which stores instructions to be followed by VSM microprocessor 152 and can also store data collected from the various physiological sensors used with the VSM. In the embodiment of the present invention illustrated in FIG. 1, a temperature sensor 86 and pulse oximeter sensor 88 are connected to VSM microprocessor 152 via VSM converter 154. VSM converter 154 is preferably capable of converting analog data to digital data, and vice versa. The non-invasive blood pressure cuff (or sphygmomanometer cuff) 94 is pneumatically connected to a blood pressure pump 140 used to pressurize the blood pressure cuff 94. Blood pressure pump 140 further preferably includes, or is connected to, pressure sensors and other sensors used to obtain a blood pressure measurement. Like the pulse oximeter sensor 88 and temperature sensor 86, blood pressure sensor 140 is connected to VSM converter 154. Those of ordinary skill in the art will understand that use of fully digital sensors can eliminate the need for analog to digital conversion of sensor signals and thus eliminate the need for VSM converter 154. It will further be understood that while the illustration provided in FIG. 1 includes only sensors for measuring blood pressure, oximetry, and temperature, these sensors are provided by way of example only, and, in practice, the present invention can include more than three sensors attached to the VSM and can include any of the sensors included in the above description.

VSM microprocessor 152 is further preferably connected to the VSM display screen 82. If VSM display screen 82 is a touch sensitive screen, microprocessor can preferably not only send data to the VSM screen 82 but also receive input from the VSM display screen 82. The VSM microprocessor can further optionally communicate with an external personal computer 158 and/or an external printer 156.

The VSM preferably receives power by a line voltage connection 150 that is regulated by at least one voltage regulator 148. However, the VSM can also rely on a battery 146 as a power source. Reliance on battery power is advantageous because it allows the VSM to be highly portable. While the voltage regulator 148 is shown in FIG. 1 as being connected only to VSM microprocessor 152, it will be understood by those of ordinary skill in the art that voltage regulator 140 can be configured to produce a number of different power outputs connected to a number of different components. By way of example, the power requirements of blood pressure pump 140 are likely to be very different than the power requirements of the VSM microprocessor 152. Accordingly, though not illustrated in FIG. 1, separate power connections from the blood pressure pump 140 and the microprocessor 152 to the voltage regulator 148 would likely be necessary.

The VSM 80 further preferably includes an RF transceiver/network interface 144 that allows the VSM to both receive data wirelessly as well as be connected to networks of other computing devices.

Figure 2:
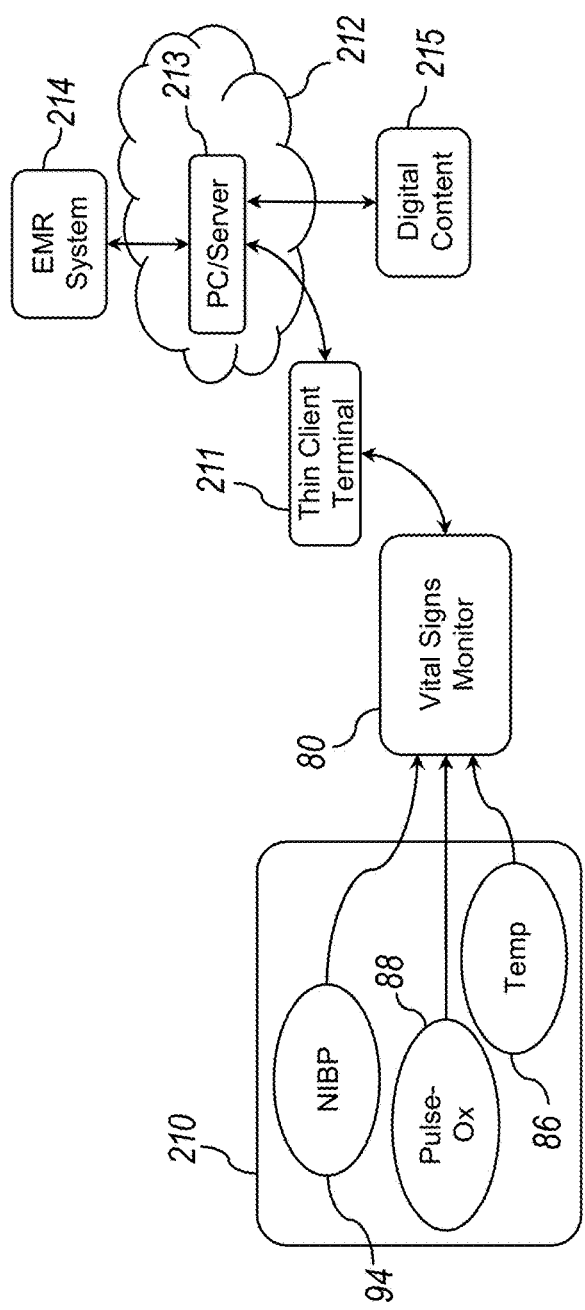
FIG. 2 depicts a flow diagram illustrating one method of moving and/or storing information collected by the vital signs monitor of the present invention.
Figure 3:
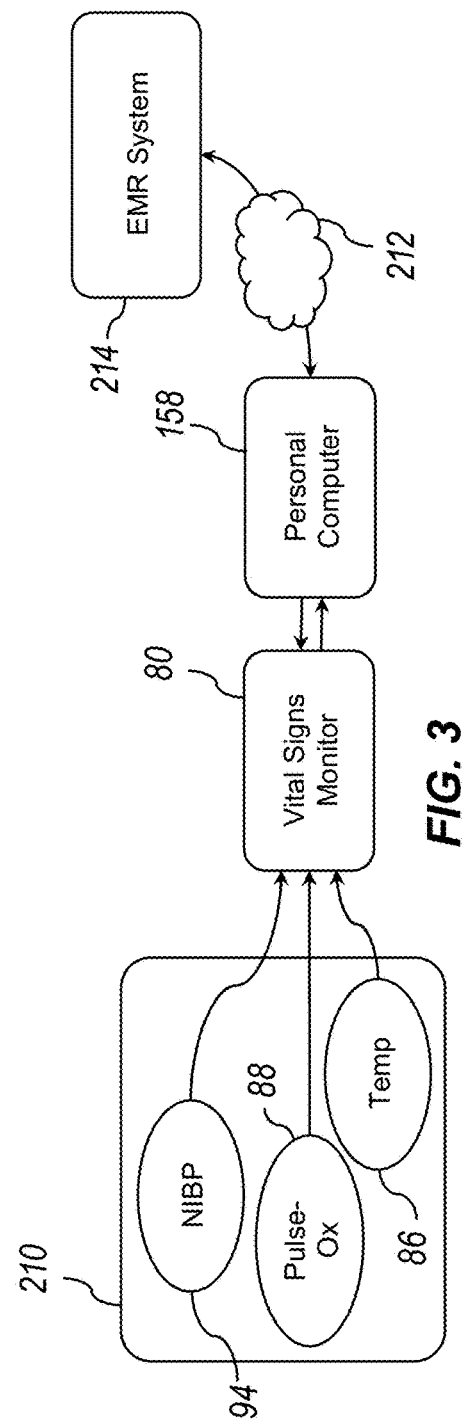
FIG. 3 depicts a flow diagram illustrating one method of moving and/or storing information collected by the vital signs monitor of the present invention.

In FIG. 2-3 there are shown flow diagrams illustrating data movement between various parts of the present invention. In each of FIG. 2-3 a sensor suite 210 illustratively shown as comprising a noninvasive blood pressure sensor 94, a pulse oximeter sensor 88, and a temperature sensor 86, sends data to the vital signs monitor 80 of the present invention. It will be understood, however, that while sensor suite 210 in FIG. 2-3 includes only sensors for measuring blood pressure, oximetry, and temperature, these sensors in the sensor suite 210 are provided by way of example only, and, in practice, the sensor suite 210 can include more than three sensors attached to the VSM and can include any of the sensors included in the above description.

EMR system 214 as depicted in FIG. 2-3 includes the electronic medical record system of the facility in which VSM 80 is located, and for purposes of FIG. 2-3 can also include the practice management system of the practice in which the VSM 80 is located. The cloud figure shown in FIG. 2-3 is intended to represent the Internet or other communication system (e.g., LAN, WAN, and the like) 212 by which digital information can be moved to a location or locations within a veterinary clinic or remotely located from the veterinary clinic.

In FIG. 2 is shown an embodiment of the present invention in which the VSM 80 includes software and appropriate hardware that allow the VSM to communicate directly with the EMR system 214. Such an arrangement is desirable in certain instances because it allows physiological measurements obtained using sensor suite 210 to be directly transferred to a patient's electronic medical record using only the VSM. FIG. 2 further illustrates one approach by which the Internet or other communication system 212 can be structured and used to efficiently move data from the VSM 80 to the EMR system 214. Specifically, in FIG. 2, the VSM interfaces with a thin client terminal 211. In turn, the thin client terminal, receives information and transmits information to the PC/server 213, which processes information received from the VSM 80 via the thin client terminal 211 and sends this information back to the VSM 80 via the thin client terminal 211 or else sends the processed information on to the EMR system 214 via a network to which both the PC/Server 213 and the EMR system 214 are connected. The PC/Server 213 can also receive and/or retrieve data from the EMR system and subsequently send this data to the VSM via the thin client terminal 211. In addition to transferring data to and from the EMR system 214, FIG. 2 also illustrates transfer of digital content 215 to and from the VSM. Digital content 215 can include training and other multimedia content described above as well as the ability of the user to use the VSM to purchase products and supplies as also described above. It will be noted, however, that use of a thin client terminal 211 is not required in all embodiments of the present invention and further that Internet or other communication system 212 as illustrated in FIG. 2 is not required to include the use of PC/Server 213. Rather, this is only one exemplary method of accomplishing communication between the VSM 80 and the EMR system 214.

FIG. 3 is largely identical to FIG. 2, however, in FIG. 3 a personal computer 158 serves as a connection point between VSM 80 and the EMR system 214. Thus, in the embodiment of the present invention illustrated in FIG. 3, the VSM does not need to include the software and hardware necessary to communicate with the EMR system 214. Rather, this software and appropriate hardware is located on the personal computer 158. While data obtained using the sensor suite 210 are initially handled by the VSM 80, the ultimate communication of this data to the EMR system 14 is handled by the personal computer 158.

Figure 4:
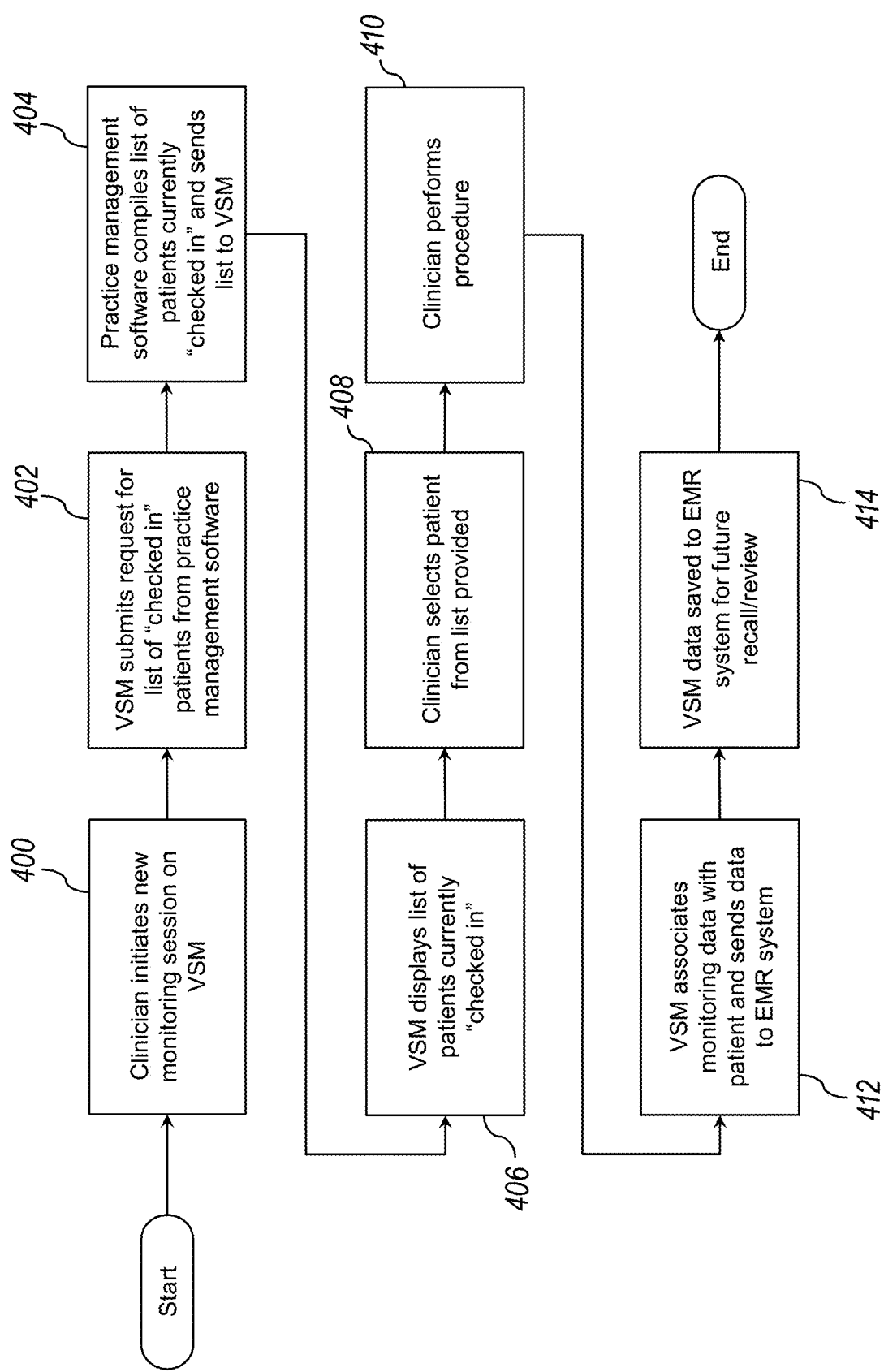
FIG. 4 depicts a flow diagram depicting steps involved in using one embodiment of the vital signs monitor of the present invention to streamline workflow and communication data to an electronic medical record system.

Turning now to a description of FIG. 4, there is shown a flow diagram depicting the steps included in one embodiment of the present invention in which the VSM is capable of communicating with the practice management software and EMR system of a veterinary practice. In this embodiment, a clinician (e.g., veterinarian, veterinarian's assistant, or the like) first initiates a new monitoring session 400 on the VSM by selecting the appropriate option using the VSM display screen. When a new monitoring session is initiated the VSM communicates with a server/database that houses the practice management software of the practice in which the VSM is located and requests a current list of patients who are "checked in" at the practice 402. This communication between the practice management server/database and the VSM is preferably accomplished using the Internet or other type of communications network outlined in the above description. Once the request from the VSM is received, the practice management software preferably compiles a list of checked in patients 404 and formats this list for display on the VSM. The list is then sent to the VSM 404 where it is displayed 406 to the clinician using the VSM. The clinician can then use the touch-sensitive screen of the VSM, or other input means such as a keyboard connected to the VSM, to select the patient that the clinician is treating or examining from the VSM display. The clinician can then begin the procedure or examination while the VSM logs the patient's identity and begins recording physiologic monitoring data and associates this data with the patient on which a procedure or examination is being performed 410, 412. Once the clinician is finished with the procedure or examination, the clinician uses the VSM interface to end the monitoring session. When the monitoring session is ended, the VSM communicates with a server/database that houses the EMR system of the practice and sends a copy of the monitoring data to the EMR system for storage and later recall or review 414. It will be noted that in this example the EMR software and practice management software could be separate software packages housed at optionally separate locations or could alternatively be part of a single integrated software system. It will further be noted that FIG. 4 is illustrative of only one possible method of using the VSM of the present invention to increase ease and efficiency of care delivery and numerous other methods and variations exist that are included within the scope of the present invention.

Figure 5:
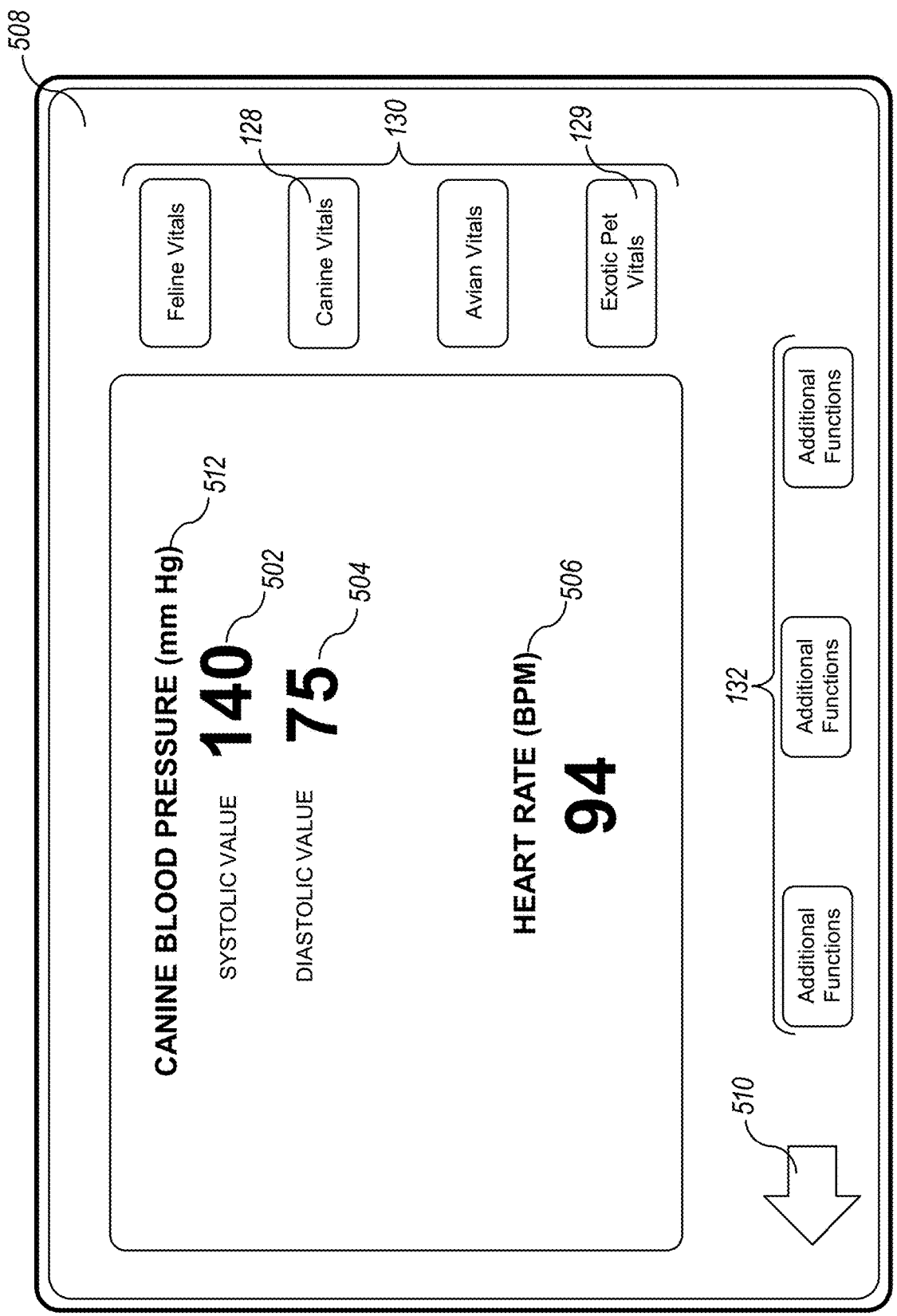
FIG. 5 depicts an exemplary vital signs monitor display screen layout and options.

In FIG. 5, there is shown one example of a display screen layout as it might appear on the VSM of the present invention. In this embodiment, a touch-sensitive screen 508 is used. A number of preprogrammed vital signs collection options 130 appear at the left side of the screen. In this example, only blood pressure 512 and heart rate 506 are displayed, though it will be understood that other parameters included in this disclosure (e.g., temperature, patient identification information, etc.) could also be shown on the display screen. When one of the preprogrammed options is selected the VSM screen displays which option was selected and the software of the VSM selects the appropriate algorithms to ensure that the measurements are as accurate as possible. In the example shown in FIG. 5, the preprogrammed "Canine Vitals" option 128 was selected. Accordingly, Canine Blood Pressure is displayed prominently on the screen, and the VSM software also selects the canine blood pressure and heart rate algorithms. The VSM can also optionally check to ensure that the appropriately sized blood pressure cuff is connected to the VSM prior to initiating blood pressure measurement. In this case, the canine blood pressure cuff could include a digital or other identification means that can be used by the VSM processor to ensure that an appropriately sized blood pressure cuff is used. Once size of blood pressure cuff is verified the cuff is inflated, a blood pressure measurement is taken, and the systolic 502 and diastolic 504 values are displayed to the VSM user. The display screen can also include areas for additional functions 132 that can be used to perform any of the above-described functions of the VSM. For example one additional function might allow the user to send the data to his or her electronic medical record system for storage. Yet another additional function might allow the user to retrieve and display previously recorded data. Navigation through the various features of the VSM can be accomplished using navigation options, such as that shown as 510 in FIG. 5. It will be noted that in certain embodiments and with certain functions, the VSM will produce different results that those pictured in FIG. 5. For example, if one were to select the "Exotic Pet Vitals" 129 option the VSM could then bring up an additional menu, allowing the user to select between various exotic pets (e.g., reptile, ferret, etc.).

Figure 6:
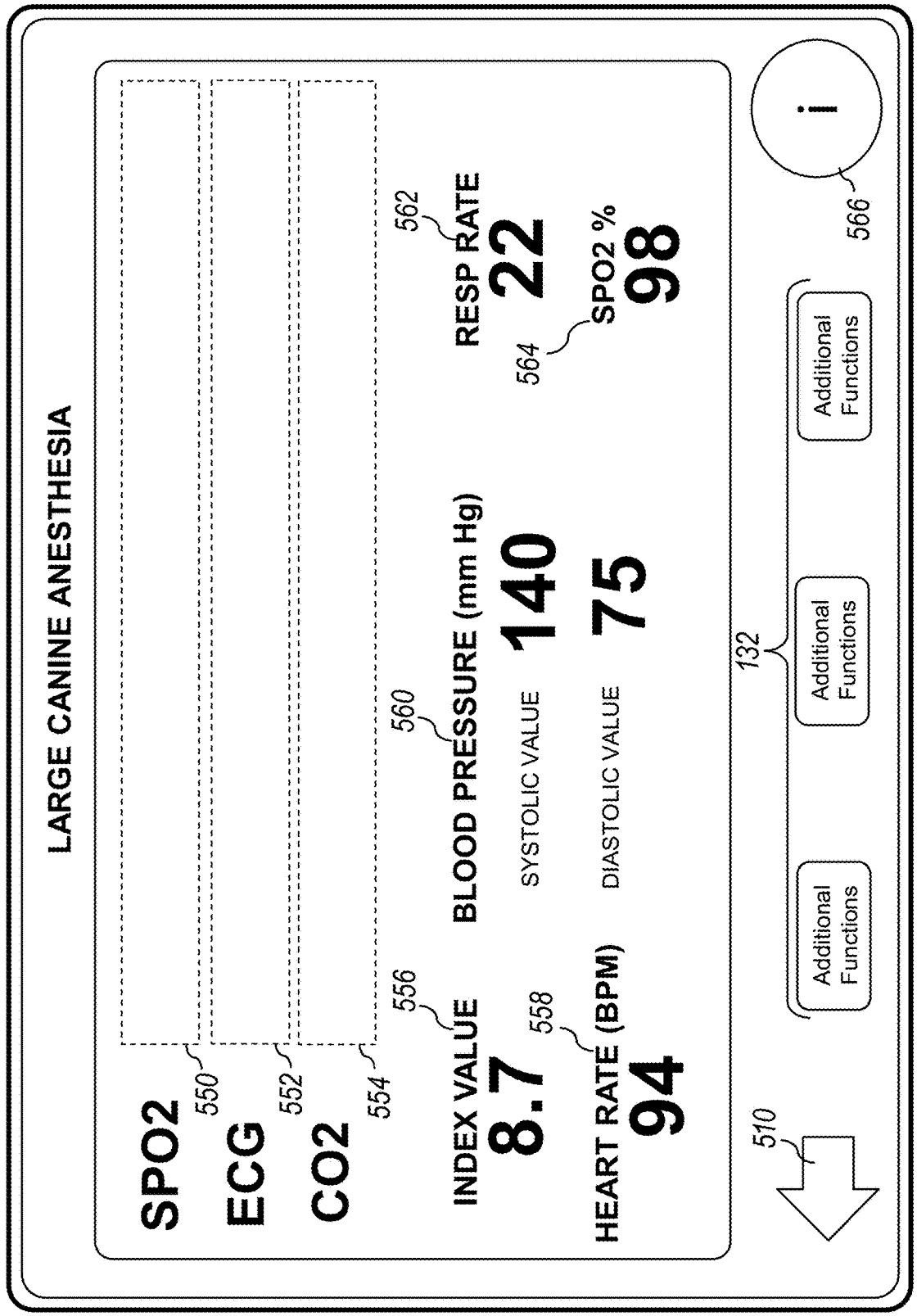
FIG. 6 depicts another exemplary vital signs monitor display screen layout and options.

In FIG. 6 there is shown one example of how the VSM of the present invention might display data while performing vitals signs monitoring during a procedure that involves the use of anesthetic. In this example a user-customized setup for large canine is shown. Accordingly, it is assumed that the user has chosen which parameters to display as well as set appropriate desired alarm limits for these parameters. The setup includes fields for displaying a blood oxygenation waveform 550, ECG waveform 552, and CO2 waveform 554. It also includes values for the above-noted parameter index 556, heart rate 558, blood pressure 560, respiratory rate 562, and percentage of blood oxygenation 564. In addition, there is shown an information icon 566. In certain embodiments of the present invention if an alarm limit is reached, the information icon can be selected and the VSM will then display recommendations for addressing the cause of the alarm. For example, if low blood pressure is the cause of the alarm, the information icon can be selected, and the user can be instructed to administer an increased volume of intravenous fluids.

As shown in FIGS. 7 and 8 some versions of VSM 80 may also include subroutines and software associated with a method of using a pre-procedure checklist. In general, the pre-procedure checklist provides functionality for increasing safety awareness and allowing clinics to track compliance with such checklists. The pre-procedure checklist provides a formalized quality check process which helps reduce errors and promotes consistency. Along with improving patient safety, usage of the pre-procedure checklist creates a greater sense of confidence in that the process is completed accurately and thoroughly, which in turn has a positive impact on health outcomes. Usage of the pre-procedure checklist can also reduce the time taken by staff to troubleshoot problems that might otherwise point to a technical malfunction of the equipment.

The pre-procedure checklist includes one or more checklist parameters, whereby the user is required to review and check a box or otherwise acknowledge each checklist parameter. In some versions of VSM 80, the full functionality of VSM 80 is suspended or locked until the user acknowledges each checklist parameter. In these versions of VSM 80, upon acknowledgement of every checklist parameter, VSM 80 becomes unlocked and the user is free to proceed using VSM 80 as desired. In other versions of VSM 80, functionality is not dependent on the user acknowledging the checklist parameters, but merely a reminder screen where the user is able to "exit" or close without acknowledgements.

Some versions of the pre-procedure checklist require the user's initials or other personal identifying information as part of the overall acknowledgement of the satisfaction of each checklist parameter. An input box, text box, camera, or otherwise similar functionality is provided to allow the user to enter the personal identifying information into VSM 80 to be stored. Some versions of VSM 80 output the personal identifying information and checklist information, potentially along with other system information such as a timestamp, at the end of the procedure. This information may be printed via external printer 156, stored in VSM memory 142, transferred into EMR system 214, or any other similar method of storing the information for later review, confirmation, or use.

Checklist parameters may be entered into VSM memory 142 by an administrator to customize the pre-procedure checklist, or the checklist parameters may be static and pre-programmed into VSM memory 142.

The following is a non-exhaustive list of example checklist parameters which may be presented to a user of VSM 80:
Perform a leak test on the anesthesia machine;
Check that the Adjustable Pressure Limiting (APL) valve is open on the anesthesia machine;
Confirm that the carbon dioxide absorbent material is not expired;
Calculate intra-op drugs;
Calculate emergency drugs;
Confirm vaporizer is filled;
Check the O2 supply; and
Check the patient's past complications.

In addition to the above, the pre-procedure checklist method may also include functionality to prompt the user regarding checklist parameters inputted by a pervious user or by an administrator. For example, two additional "slots" or checklist parameters may be user edited and entered, while other checklist parameters may be embedded in the underlying software. In this way, the checklist parameters may include at least one static or permanent checklist parameter along with at least one dynamic or editable checklist parameter.

FIG. 7A depicts a pre-procedure checklist graphical user interface (GUI) 216 displayed on display screen 82. Pre-procedure checklist GUI 216 outputs checklist parameters to the user along with input features to allow the user to check or otherwise indicate when each checklist parameter has been completed. As shown in FIG. 7A, an exemplary checklist parameter 218 is displayed in an area of pre-procedure checklist GUI 216 proximate an input box 220. Checklist parameter 218 is retrieved from an internal database or memory such as VSM memory 142 and rendered on display screen 82 along with input box 220. Input box 220 is initially rendered blank when pre-procedure checklist GUI 216 is loaded on display screen 82. Input box 220 awaits a check or other input from the user to signify checklist parameter 218 has been satisfied. An "X" is shown within input box 220 to indicate the user representing checklist parameter 218 has been completed.

As shown in FIG. 7A, an exemplary personal identifying information input box 222 is rendered on display screen 82 next to a prompt for the user's personal identifying information, shown as "Enter initials with keyboard." This personal identifying information could be the user's initials or a thumbprint or an e-signature, or any other information for identifying the user.

Once the user has indicated each checklist parameter has been satisfied and has entered personal identifying information, the user actuates an actuation element 224, shown in FIG. 7A as a graphical button with "Submit" displayed thereon. Upon submission, some versions of the logic software associated with pre-procedure checklist GUI 216 verifies the user has entered information for each input box 220 and personal identifying information input box 222, which indicates every checklist parameter has been satisfied and personal identifying information has been entered. If the logic software associated with pre-procedure checklist GUI 216 determines at least one input box 220 or personal identifying information input box 222 is empty/unchecked, pre-procedure checklist GUI 216 continues to be presented to the user until each input box 222 is checked and personal identifying information has been entered. In this manner, the user is prevented from accessing the underlying functionality of VSM 80 until the pre-procedure checklist has been completed and the user has provided personal identifying information. If the logic software associated with the pre-procedure checklist GUI 216 determines all of the inputs are satisfied, the underlying functionality of VSM 80 is unlocked and presented to the user. The logic software also stores the user's personal identifying information, potentially along with information such as a timestamp, in the internal storage of VSM 80 for later retrieval or storage in ERM system 214.

Figure 7B:
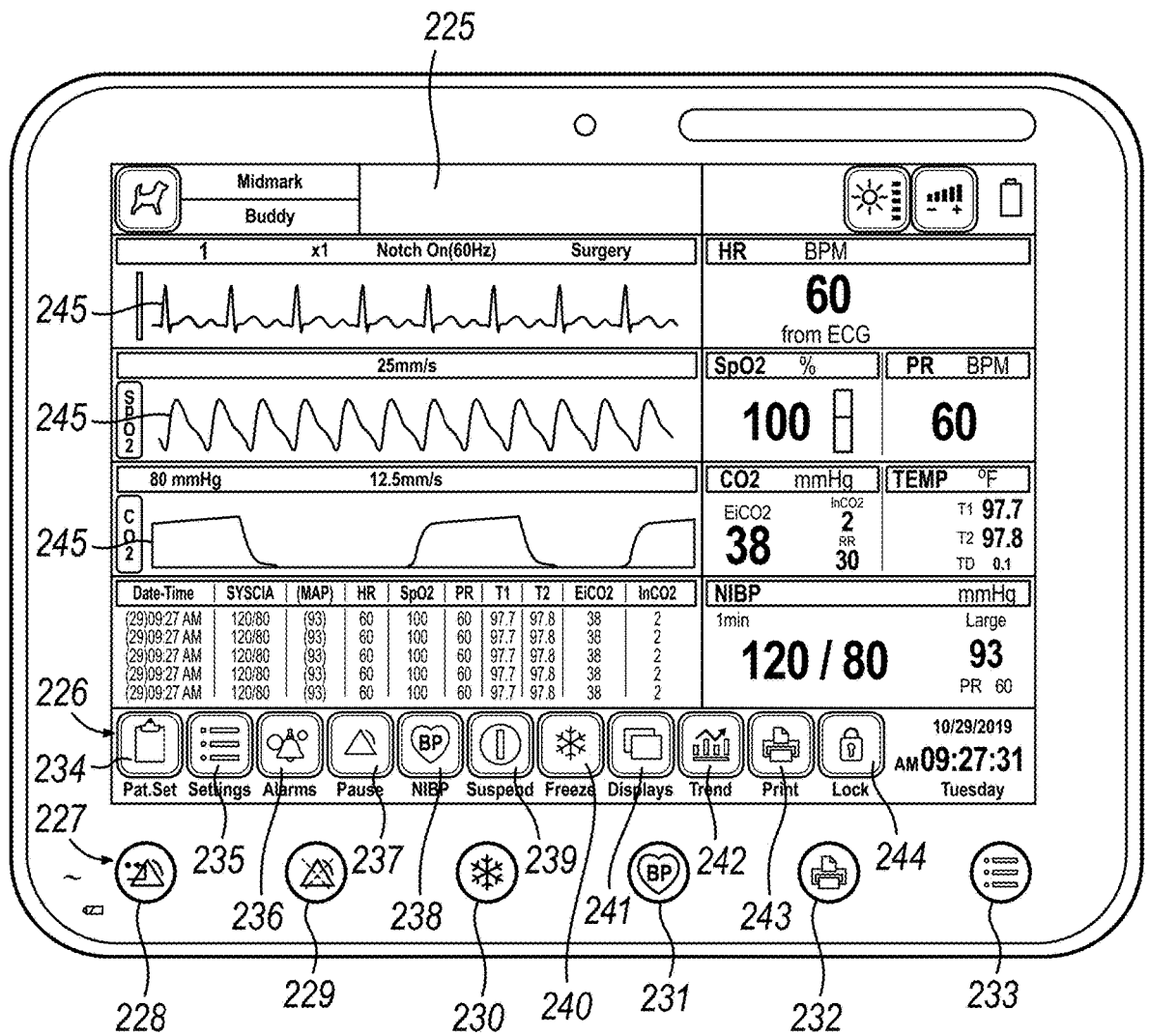
FIG. 7B depicts another exemplary vital signs monitor display screen layout and options.
Figure 7C:
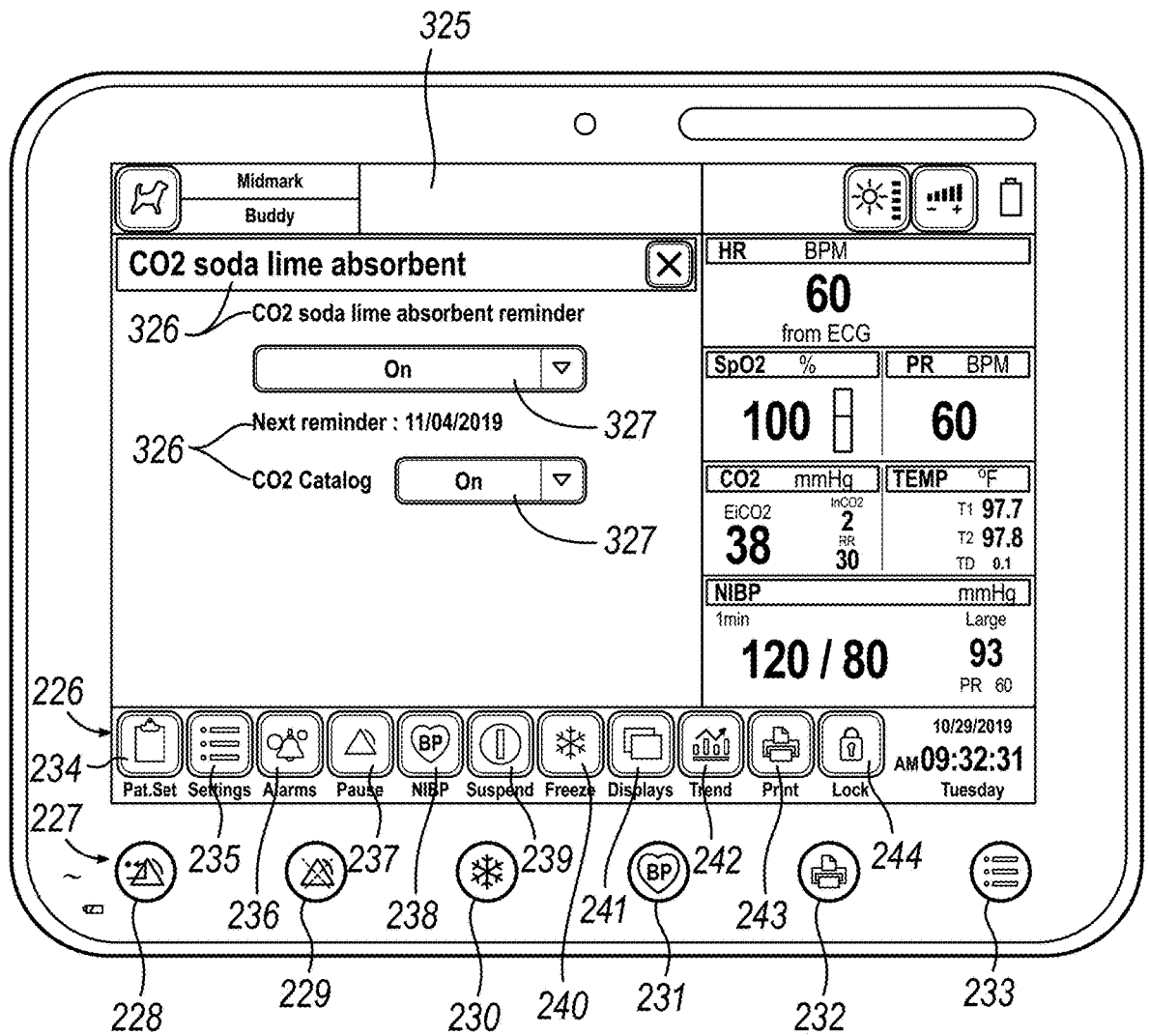
FIG. 7C depicts another exemplary vital signs monitor display screen layout and options with respect to a $CO_2$ soda lime absorbent reminder graphical user interface.

FIGS. 7B and 7C depict other exemplary versions of a graphical user interface for use with VSM 80. As shown in FIG. 7B, a graphical user interface (GUI) 225 is provided on VSM 80 with various vital signs waveforms, data, and buttons for attending to the patient. GUI 225 may include and display one or more waveforms 245 in a scrolling method to update continuously. GUI 225 may also include and display virtual buttons 226 which are provided for actuation by a user. In some versions of VSM 80, GUI 225 includes virtual buttons 226 relating to updating patient settings, settings in general, actuating and attending to alarms, pausing various features of VSM 80, attending to blood pressure features, suspending various features, freezing waveforms for further inspection, updating the display or changing GUI 225, displaying trends or trendline information, printing the waveforms or various vital signs, and locking the screen.

With specific reference to FIG. 7B, VSM 80 a patient setting button 234 may be provided for setting up a patient with admit or discharge information or various patient data. A settings button 235 may also be provided, whereby settings button 235 is pressed to open a settings menu where the user may set preferences for various parameters and access major functions of VSM 80. An alarms button 236 may also be provided, whereby alarms button 236 is pressed to open an alarm setup menu whereby the user may set alarm limits for the parameters within the monitor. An alarm pause button 237 may be provided, whereby pressing alarm pause button 237 temporarily pauses the audio portion of the current alarms, though the visual portion may still be active. The visual portion may include flashing lights and the display of an alarm message. Depending in the user presets, the alarm will return to normal after a predetermined time range. A NIBP button 238 may be provided, whereby pressing NIBP button 238 manually starts the NIBP measurement, with the NIBP measurement automatically stopping once completed. A user may press NIBP button 238 again before completing the NIBP measurement process to stop it immediately. Pressing and holding NIBP button 238 may provide access to a screening mode. A suspend button 239 may also be provided, whereby a user may press suspend button 239 to stop all waveform and parameter testing via VSM 80. A freeze button 240 may also be provided, whereby a user presses freeze button 240 to stop movement of the waveform across the screen so the user may analyze the current waveform more carefully. Freeze button 240 may be pressed again to restart the movement and in some confirmations the screen will remain frozen until the user presses freeze button 240 again. A display button 241 may be provided, whereby a user presses display button 241 to toggle through all the different display modes offered by the monitor, which may include normal, enlarged display, 7-lead ECG with numerical data, IBP, and multigas. A trend button 242 may also be provided, whereby a user presses trend button 242 to open a menu to review graphic, tabular, and/or NIBP trends. A print button 243 may also be provided, whereby a user presses print button 243 to print current patient information. VSM 80 may be configured to print a preset amount of minutes. Print button 243 may be pressed again to stop printing before the preset amount of time. A screen lock button 244 may also be provided, whereby a user presses screen lock button 244 to lock the touch screen function of GUI 225 of VSM 80 to prevent accidental changes to settings. GUI 225 may change screen lock button 244 to a different icon (e.g. an unlock icon) once it is pressed. Pressing screen lock button 244 will unlock GUI 225 and as a result, GUI 225 may change back to the original icon (e.g. a lock icon).

VSM 80 may also provide physical buttons 227 which may provide similar functionality as virtual buttons 226, though physical buttons 227 are provided along the front enclosure and outside of GUI 225. Physical buttons 227 may include an alarm reset button 228, an alarm pause button 229, a freeze button 230, a start/stop BP button 231, a start/stop printing button 232, and a settings button 233. Alarm reset button 228 may have similar functionality as alarms button 236 and/or alarm pause button 237 and may be configured to silence an audible alarm provided by VSM 80 in response to various triggers. Alarm pause button 229 may have similar functionality as alarms button 236 and/or alarm pause button 237 and may be configured to pause the audible alarm for an interval designated by the user. In some configurations of VSM 80, freeze button 230 may have similar functionality as freeze button 240 and may be configured to freeze a waveform when the waveform is sweeping across the screen. One press of freeze button 230 freezes the waveform while a second press of freeze button 230 unfreezes the waveform sweep. In some configurations of VSM 80, start/stop BP button 231 may have similar functionality as NIBP button 238 and suspend button 239 and may be pressed to start blood pressure measurement and pressed again to stop the measurement. If start/stop BP button 231 is not pressed to stop blood pressure measurement, the monitor will stop automatically when the measurement is completed. In some configurations of VSM 80, start/stop printing button 232 may have similar functionality as print button 243 and may be pressed to start printing and pressed again to stop printing. If start/stop printing button 232 is not pressed to stop printing, VSM 80 will stop printing automatically after printing out 8 seconds worth of data/waveform. VSM 80 may also be set to print at user selected intervals. In some configurations of VSM 80, settings button 233 may have similar functionality as settings button 235 and may be configured to open the settings menu where the user may set preferences for various parameters and access major functions of VSM 80.

As shown in FIG. 7C, a graphical user interface (GUI) 325 may be provided to remind the user to replace the CO2 soda lime associated with VSM 80. Soda lime is responsible for the elimination of carbon dioxide (CO2) in rebreathing circuits. When exhausted, CO2 accumulates in the circuit and is rebreathed by the patient, causing respiratory acidosis that can be harmful. Soda lime is a key element in a rebreathing circuit. As with most anesthesia equipment, inappropriate use can be harmful, or even lethal, for the patient. Thus, in one embodiment of VSM 80, reviewing and confirming CO2 soda lime associated with VSM 80 is incorporated into the pre-procedure checklist whereby a user cannot access additional functionality of VSM 80 until the user checks an input feature signifying the user has checked the CO2 soda lime associated with VSM 80. GUI 325 is one example of a graphical interface provided to the user of VSM 80. In GSM 325, various output fields 326 and input fields 327 are provided to prompt the user to consider the CO2 soda lime associated with VSM 80 as well as set a future reminder for future considerations.

Figure 8B:
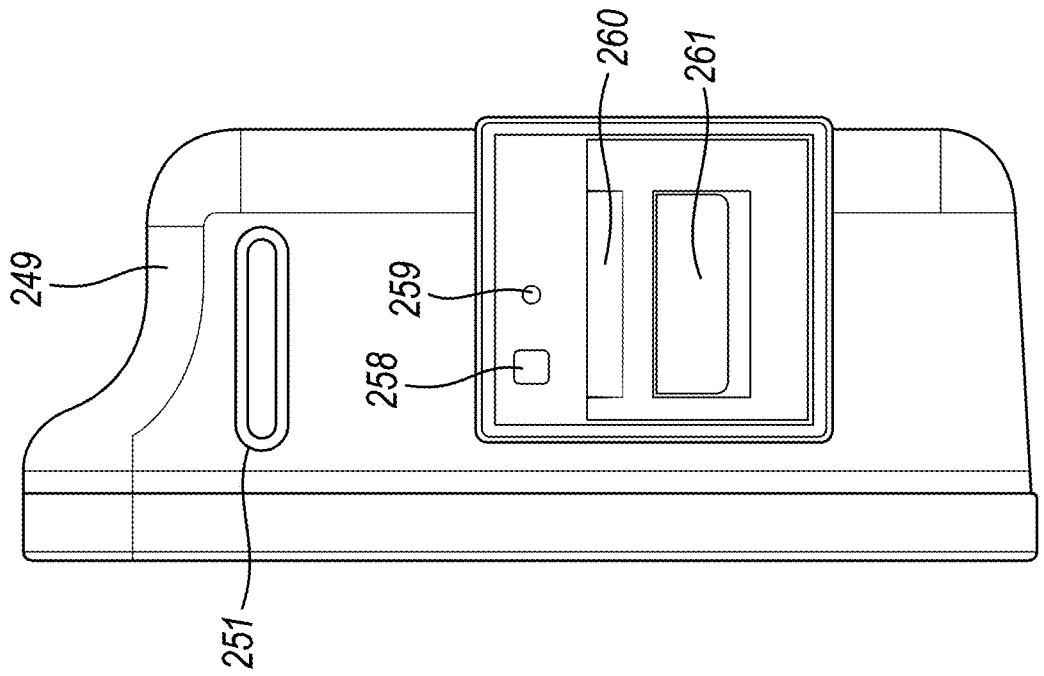
FIG. 8B depicts a second side view of the exemplary vital signs monitor of FIG. 8A.
Figure 8A:
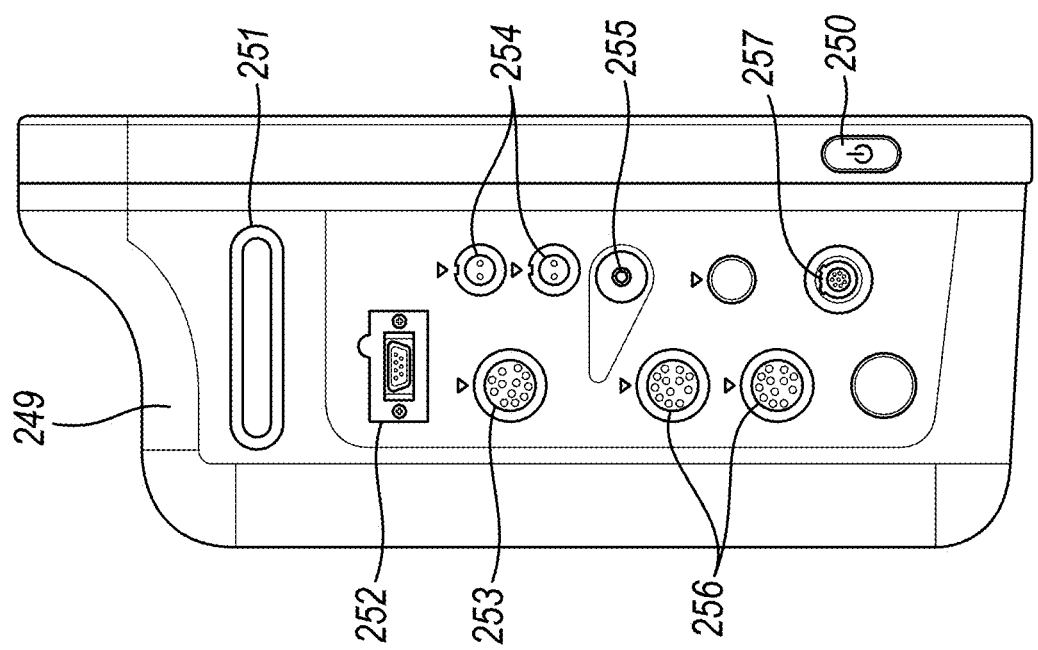
FIG. 8A depicts a first side view of an exemplary vital signs monitor.
Figure 8C:
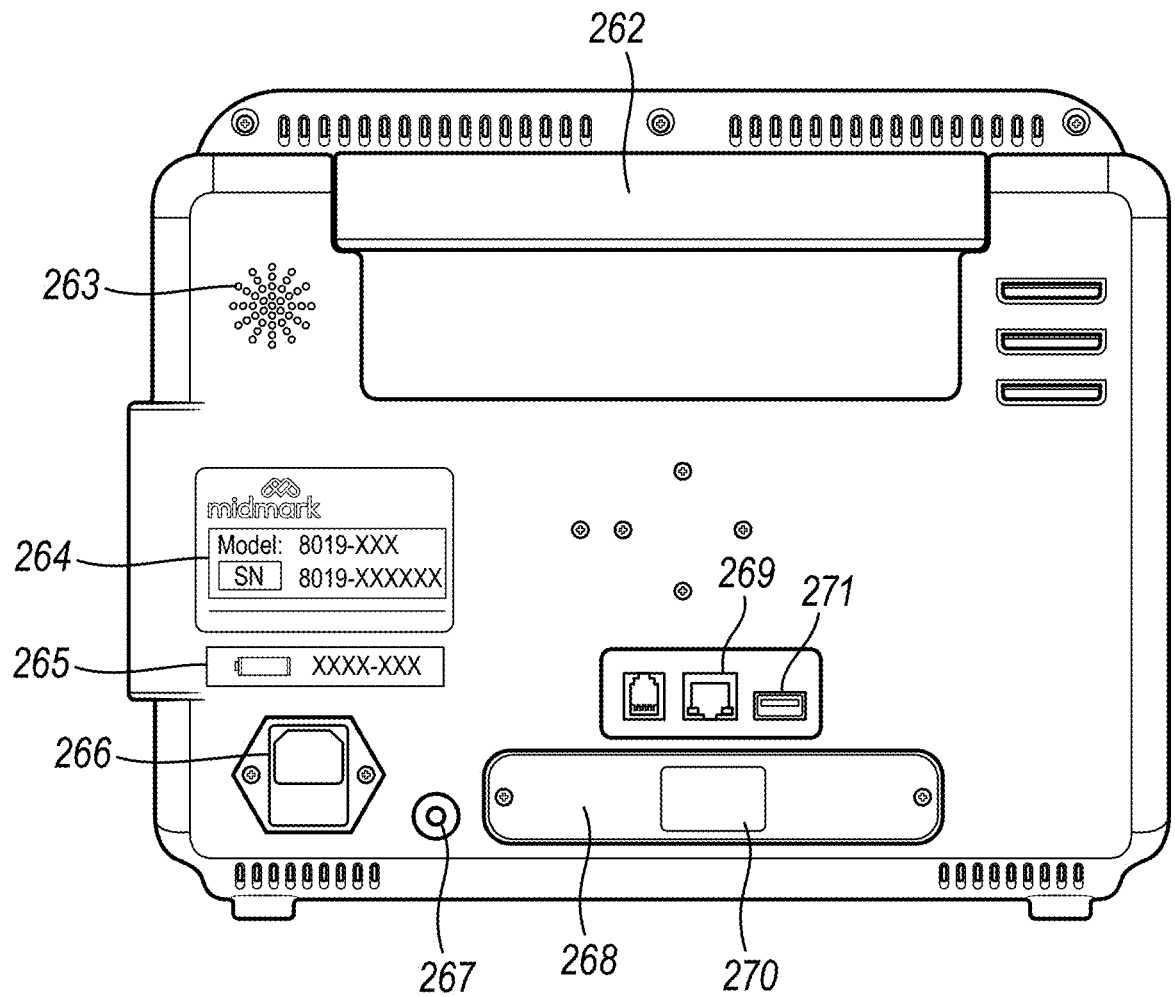
FIG. 8C depicts a rear view of the exemplary vital signs monitor of FIG. 8A.

FIGS. 8A-8C depicts an exemplary housing 249 for VSM 80. Housing 249 may incorporate, define, or include various ports, indicators, buttons, or receptacles for connecting peripherals or I/O devices to VSM 80.

As shown in FIG. 8A, VSM 80 may include a power switch 250. When VSM 80 is connected to a wall socket or there is enough battery power, power switch 250 is configured to turn VSM 80 on or off when actuated. After VSM 80 is turned off, battery 146 continues to charge if VSM 80 is connected to AC power.

As shown in FIGS. 8A and 8B, VSM 80 may include an alarm indictor 251 configured to light up or signal when there is an alarm. Some versions of alarm indicator 251 incorporate LED lights projecting out from housing 249. The alarm signals projected by alarm indicator 251 may be configured by the user and may provide different colors for different severities of the issue. For example, for physiological alarms, alarm indicator 251 may project solid red or flash red if the measured physiological element is significantly outside of the associated parameters and may project solid yellow or flash yellow if the measured physiological element is slightly outside of the associated parameters.

As shown in FIG. 8A, VSM 80 may include various receptacles for connecting to various elements. For example, VSM 80 may include an SPO2 receptacle 252 for receiving a SpO2 extension cable extending from an SpO2 feature such as Pulse-Ox 88; an ECG receptacle 253 for receiving an ECG cable; a temperature receptacle 254 for receiving a temperature cable extending from a temperature probe such as temperature sensor 86; an NIBP receptacle 255 for receiving an NIBP inflation hose extending from an NIBP element such as NIBP Cuff 94; an IBP receptacle for receiving an IBP cable; and a CO2 receptacle for receiving mainstream or sidestream CO2 or AG module accessories.

As shown in FIG. 8B, VSM 80 may include print capabilities to allow a user to print out the current data or waveform. For example, VSM 80 may include a print button 258 configured to start printing the current data/waveform when pressed a first time and stop printing when pressed again. VSM 80 may include a printer indicator light 259 to indicate VSM 80 is set to print (i.e. light on) or not print (i.e. light off). VSM 80 may include a printer 260 which is an internal built in printer disposed inside housing 249 with a slot or shoot for allowing the printed ribbon or paper to be expelled from VSM 80 and housing 249. To that end, VSM 80 may include a printer door latch 261 to allow a user to open housing 249 to access the internal printer paper compartment.

As shown in FIG. 8C, VSM 80 may include a handle 262 for helping to facilitate handling and moving VSM 80. VSM 80 may include a speaker 263 for facilitating alerts, alarms, or other audible sounds. VSM 80 may include a label 264 for displaying indicia to the user such as model number and manufacturer. VSM 80 may include a fuse indicia 265 for displaying information regarding the fuse used in VSM 80. VSM 80 may include an AC power connector 266 for receiving a power cord and providing power to VSM 80 therethrough. VSM 80 may include a grounding port 267. VSM 80 may also include a battery compartment 268 for storage of battery 146. For communication and data transfer, VSM 80 may include a network connection port 269 and/or a USB port 271.

Figure 9:
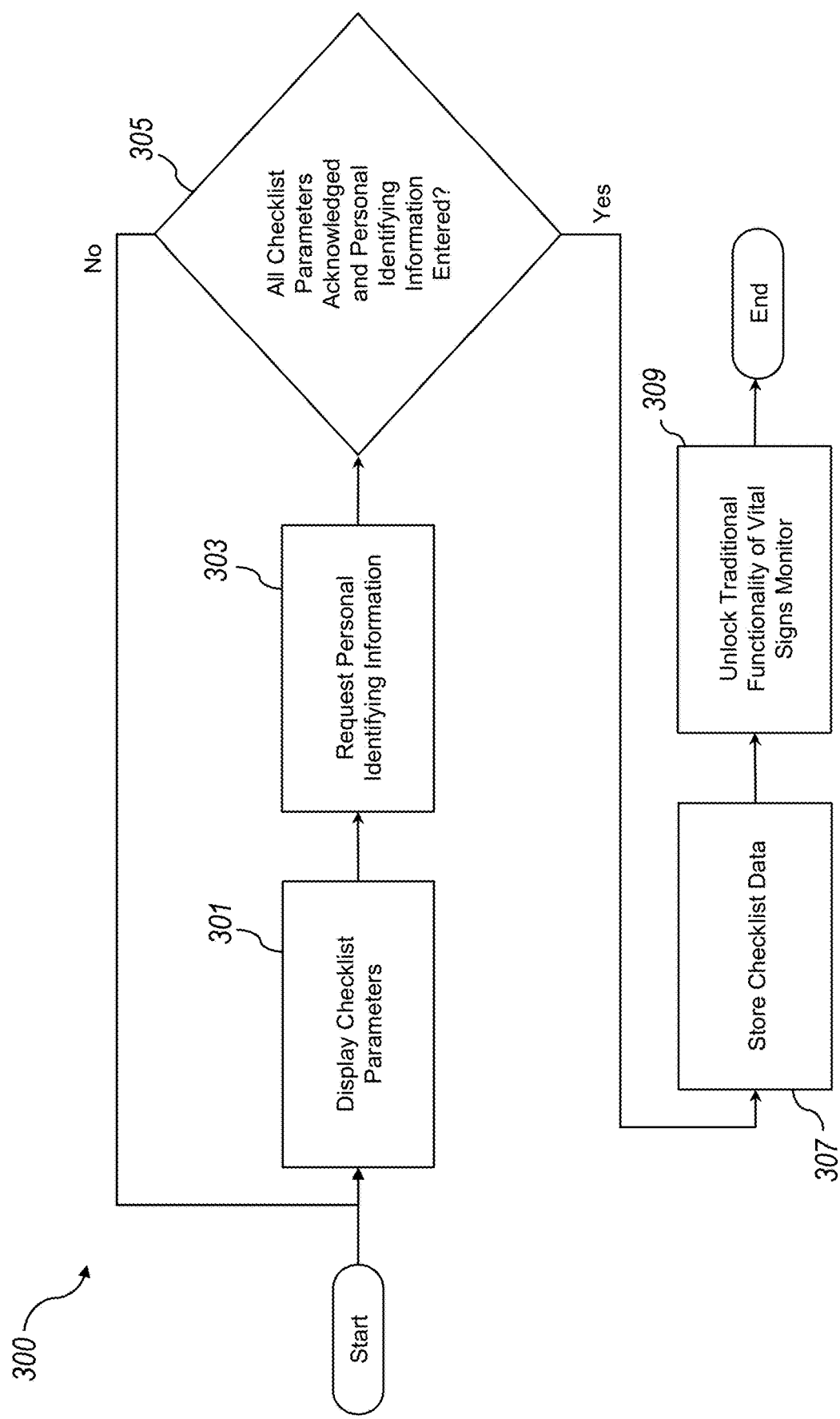
FIG. 9 depicts a flow diagram of steps involved in one embodiment of a pre-procedure checklist method of the vital signs monitor of the present invention.

FIG. 9 depicts an exemplary pre-procedure checklist method 300. Pre-procedure checklist 300 begins with a step 301, whereby all of the checklist parameters are displayed to the user. The checklist parameters may be stored in a database or similar memory such as VSM memory 142. In some embodiments of method 300, a graphical input box such as a checkbox is displayed next to each checklist parameter to allow the user to acknowledge which checklist parameters have been completed. Thereafter, step 301 proceeds to a step 303.

In step 303, the user's initials or other personal identifying information is requested, possibly via an input box or a signature block or some other interface element. The user is prompted to enter this information to continue on to the traditional functionality of the underlying VSM 80 and to allow VSM 80 to log who acknowledged each checklist parameter was completed. Once the user is prompted to enter personal identifying information, step 303 proceeds to a step 305. Step 303 may be combined with step 301 in that in some embodiments of the pre-procedure checklist all of the checklist parameters are displayed along with and at the same time as a request for personal identifying information. The transition from step 303 to step 305 may be actuated by a user pressing or actuating a graphical user interface button or other actuation element.

Step 305 determines whether the user has acknowledged all of the checklist parameters, possibly by checking a checkbox next to each parameter or otherwise indicating completion of each parameter via an input. Step 305 also determines whether the user has entered personal identifying information in accordance with the prompt of step 303.

If step 305 determines the user has not acknowledged all of the checklist parameters or has not entered personal identifying information, step 305 proceeds back to step 301. Thus, step 305 prevents a user from accessing any of the traditional vital signs monitor functionality until each checklist parameter is acknowledged and personal identifying information is provided.

If step 305 determines that the user has acknowledged all of the checklist parameters and has entered personal identifying information, step 305 proceeds to a step 307. In step 307, information regarding the user's acknowledgement of completing the pre-procedure checklist, along with the personal identifying information, is stored for later retrieval. Thereafter, step 307 proceeds to a step 309. In step 309, the traditional vital signs monitor functionality is "unlocked" and provided to the user and thereafter method 300 proceeds to end.

In an alternative version of method 300, step 305 is omitted and the user is free to access the underlying traditional functionality of the vital signs monitor regardless of whether the checklist parameters are acknowledged, or the user has entered personal identifying information. This version of method 300 does not lock the user out of the functionality of the vital signs monitor and merely provides the checklist as "best practice" or suggestions to the user.

It will be apparent to those skilled in the art that various modifications and variations can be made to the present invention without departing from the spirit and scope of the invention as set forth in the above description. Thus, it is intended that the present invention cover the modifications and variations of this invention provided they come within the scope of the invention and its equivalents.

What is claimed is:

1. A method comprising:
   (a) preventing a user from accessing a set of features of a veterinary vital signs monitor;
   (b) displaying a plurality of checklist parameters in conjunction with an associated checklist parameter input element on a display screen of the veterinary vital signs monitor, wherein each checklist parameter input element is configured to be selectively acknowledged by the user;
   (c) displaying a personal identifying information input element on the display screen, wherein the personal identifying information input element is configured to be selectively acknowledged by the user by entering a personal identifier;
   (d) determining every checklist parameter input element has been acknowledged by the user;
   (e) determining the user has entered the personal identifier; and (f) in response to determining every checklist parameter input element has been acknowledged by the user and determining the user has entered the personal identifier, allowing the user to access the set of features of the veterinary vital signs monitor.

2. The method of claim 1, further comprising in response to determining every checklist parameter input element has been acknowledged by the user and determining the user has entered the personal identifier, allowing the user to customize one or more checklist parameters in the plurality of checklist parameters.

3. The method of claim 2, further comprising storing the personal identifier in a memory associated with the veterinary vital signs monitor.

4. The method of claim 3, further comprising printing a report, wherein the report includes a description of each of the checklist parameters in the plurality of checklist parameters and the personal identifier.

5. The method of claim 3, further comprising storing a timestamp with the personal identifier in the memory associated with the veterinary vital signs monitor.

6. The method of claim 1, further comprising prompting the user to review an amount of CO2 soda lime associated with the veterinary vital signs monitor, wherein one of the checklist parameters in the plurality of checklist parameters is associated with reviewing the amount of CO2 soda lime.

7. A method comprising:
   (a) preventing access to a set of features of a veterinary vital signs monitor;
   (b) on a display screen of the veterinary vital signs monitor, prompting a user to acknowledge performance of a task via a task description;
   (c) on the display screen, prompting the user to enter a personal identifier; and
   (d) in response to the user acknowledging performance of the task and entering the personal identifier, allowing access to the set of features,
   wherein the task is one of:
   (i) a leak test on an anesthesia machine associated with the veterinary vital signs monitor,
   (ii) an expiration check of a carbon dioxide absorbent material associated with the veterinary vital signs monitor, and
   (iii) a volume check of an anesthesia vaporizer associated with the veterinary vital signs monitor.

8. The method of claim 7, wherein the set of features includes allowing the user to modify the task description.

9. The method of claim 7, further comprising storing the personal identifier in a memory associated with the veterinary vital signs monitor.

10. The method of claim 9, further comprising printing a report, wherein the report includes the task description and the personal identifier.

11. The method of claim 9, further comprising storing a timestamp with the personal identifier in the memory associated with the veterinary vital signs monitor.

\* \* \* \* \*